US007608249B2

United States Patent
Terreno et al.

(10) Patent No.: US 7,608,249 B2
(45) Date of Patent: Oct. 27, 2009

(54) ENHANCED SUBSTRATE IMAGING BY REVERSIBLE BINDING TO A PARAMAGNETIC COMPLEX

(75) Inventors: Enzo Terreno, Milan (IT); Silvio Aime, Milan (IT); Mauro Botta, Milan (IT)

(73) Assignee: Bracco Imaging S.p.A., Milan (IT)

( * ) Notice: Subject to any disclaimer, the term of this patent is extended or adjusted under 35 U.S.C. 154(b) by 394 days.

(21) Appl. No.: 10/492,231

(22) PCT Filed: Oct. 9, 2002

(86) PCT No.: PCT/EP02/11271

§ 371 (c)(1), (2), (4) Date: Aug. 16, 2004

(87) PCT Pub. No.: WO03/033479

PCT Pub. Date: Apr. 24, 2003

(65) Prior Publication Data

US 2004/0258618 A1 Dec. 23, 2004

(30) Foreign Application Priority Data

Oct. 11, 2001 (EP) .................... 01124440

(51) Int. Cl.
*A61B 5/055* (2006.01)
(52) U.S. Cl. .......... 424/9.365; 424/9.3; 424/9.36; 424/9.361; 424/9.363; 424/9.364
(58) Field of Classification Search .......... 424/9.364, 424/9.361, 9.36, 9.3; 600/410
See application file for complete search history.

(56) References Cited

U.S. PATENT DOCUMENTS

| 4,933,441 A | * | 6/1990 | Gibby ........................ 534/16 |
| 5,597,548 A | * | 1/1997 | Sherry et al. ................. 424/9.3 |
| 5,756,065 A | * | 5/1998 | Wilson et al. .............. 424/1.53 |
| 5,977,353 A | | 11/1999 | Argese et al. |
| 6,071,245 A | * | 6/2000 | Kohno et al. ................ 600/532 |

FOREIGN PATENT DOCUMENTS

| FR | 2 725 449 | 4/1996 |
| FR | 2 802 928 | 6/2001 |
| WO | WO/0038738 | 7/2000 |

OTHER PUBLICATIONS

Murphy, P. et al., Mag. Res. Med., 1999, 42, p. 1155-1158.*
Aime, S. et al., Chem. Eur. J., 1999, 5 (4), p. 1253-1260.*
Sherry et al., J. Biol. Chem., 1985, 260, p. 9272-9279.*
Burai et al., Mag. Res. in Med., 1997, 38, p. 146-150 (abstract).*
Bruce et al., J. Am. Chem. Soc., 2000, 122, p. 9674-9684.*
Naruse et al., Shinkei Kenkyu no Shinpo, 1994, 38(2), p. 286-300 (abstract).*
Dezortova, Child's Nerv Syst, 15, 1999, p. 408-412.*
Gong, Magnetic Reson. Imag., 1991, 9, p. 101-106 (abstract).*
Elst, Magnetic Res in Medicine, 1994, 31, p. 437-444 (abstract).*
Sappey-Marinier et al., Radiol., 1992, 183, p. 247-256 (abstract).*
PCT International Search Report for PCT/EP02/11271 dated Feb. 26, 2003.
Margerum et al.: "Gadolinium(III) D03A macrocycles and polyethylene glycol coupled to dendrimers. Effect of molecular weight on physical and biological properties of macromolecular magnetic resonance imaging contrast agents", Journal of Alloys and Compounds, vol. 249, No. 1-2, 1997.

* cited by examiner

*Primary Examiner*—Michael G Hartley
*Assistant Examiner*—Leah Schlientz
(74) *Attorney, Agent, or Firm*—Kramer Levin Naftalis & Frankel LLP

(57) ABSTRACT

The invention relates to a method for the Magnetic Resonance Imaging and Magnetic Resonance Spectroscopy Imaging of a substrate molecule different from water wherein the NMR signal is enhanced by a reversible binding of the substrate molecule to a paramagnetic chelate complex, as well as to the use of a paramagnetic chelate complex in said method and the pharmaceutical composition for use therein.

10 Claims, 5 Drawing Sheets

ENHANCED SUBSTRATE IMAGING BY REVERSIBLE BINDING TO A PARAMAGNETIC COMPLEX

This application is the national stage filing of corresponding international application number PCT/EP02/11271, filed Oct. 9, 2002, which claims priority of European Application No. 01124440.7, filed Oct. 11, 2001, all of which are hereby incorporated by reference.

The present invention relates to the Magnetic Resonance Imaging field. In particular the invention relates to a method for the Magnetic Resonance Imaging and Magnetic Resonance Spectroscopy Imaging of a substrate molecule different from water wherein the NMR signal is enhanced by a reversible binding of the substrate molecule to a paramagnetic chelate complex.

The invention also relates to the use of a paramagnetic chelate complex in said method and the pharmaceutical composition for use therein.

BACKGROUND OF THE INVENTION

The diagnostic imaging based on the Nuclear Magnetic Resonance principles, which includes the Magnetic Resonance Imaging (MRI) and the Magnetic Resonance Spectroscopy Imaging (MRSI), herein after collectively indicated as MRI, is a well established imaging method which represents a powerful tool for everyday clinical investigations.

The large majority of MRI procedures deals with the very intense water signal, the concentration of which in the human body is about 55.6 M. In most cases, $^1$H-MR images of the examined organ or body tissue correspond to a topological representations of differences in water density and/or relaxation rates of water protons into the region of clinical interest.

The contrast in these images can be augmented by the use of specific substances, known as contrast agents for MRI, modifying the relaxation times, $T_1$ and $T_2$, of water protons.

Because of their ability to affect relaxation times, many paramagnetic substances have potential as contrast agents. In practice, however, only metal complexes or cluster complexes that are paramagnetic as a result of containing one or more unpaired electrons are used as MRI paramagnetic contrast agents.

The most important class of contrast agents for MRI is represented by paramagnetic chelates, especially those containing one of the following paramagnetic ions: Gd(III), Mn(II), Fe(III) and Cr(III).

Their effect on the relaxation rate of water protons is usually assessed through the determination of their relaxivity ($r_1$), i.e. the relaxation enhancement of water protons promoted by the paramagnetic complex at 1 mM concentration, measured at a given observation frequency (often 20 MHz) and temperature (usually 39° C.).

The relaxivity $r_1$ of a given paramagnetic complex may be considered as the sum of different contributions reflecting the different interaction modalities between water protons and the paramagnetic center.

The most important of these contributions, $r_1^{is}$, directly depends on the ratio between the concentration of water bound to the given paramagnetic chelate complex and the total concentration of water, and inversely depends on the sum of the relaxation time $T_{1M}$ and the residence time $\tau_M$ of the protons of the water molecule(s) coordinated to the paramagnetic chelate complex, according to the following equation:

$$r_1^{is} = \frac{[H_2O]_{bound}}{[H_2O]_{total}} \frac{1}{T_{1M} + \tau_M}$$

In this formula $[H_2O]_{bound}$ corresponds to the concentration of the given paramagnetic complex times the number (q) of water molecules directly coordinated to the metal centre. Since in most cases q=1 and $[H_2O]_{total}$=55.6 M, for 1 mM concentration of the paramagnetic chelate, the ratio $[H_2O]_{bound}/[H_2O]_{total}$ is a fixed value ($1.8 \cdot 10^{-5}$). This means that, in the case of MR images of the water signal, this ratio cannot be increased to a greater extent.

Most paramagnetic metal complexes have been developed for MRI methods based on the resonance of $^1$H water protons: examples of said complexes and their use in conventional $^1$H water protons magnetic resonance imaging methods are reported, inter alia, in WO 00/38738, U.S. Pat. No. 5,977,353, FR 2725449, FR 2802928 and in J. Alloys and Compounds, 249(1997) 185-190.

A relatively small portion of MRI clinical applications deals with imaging of resonances of $^1$H protons other than the $^1$H water protons.

In such cases, attention has been focused on species present in relatively large amount like the fatty constituents present in many tissues (E. L. Thomas and J. D Bell in "Methods in Biomedical Magnetic Resonance Imaging and Spectroscopy", Wiley; 2000. Vol. 2, p 837-845 and references therein), or in the use of sophisticated and dedicated techniques and equipments (EP-A-370333 for the in vivo lactate visualization).

Also the acquisition of MR images of nuclei different from protons is rather uncommon in biological systems. First of all, it is not easy to find in such systems magnetically active nuclei, i.e. nuclei with nuclear spin ≠0, naturally present at sufficiently high concentration or whose enrichment in the isotope of interest is practically feasible.

Secondly, and mainly, the relaxation times of these magnetically active nuclei other than $^1$H often exceeds one second, making very time consuming the accumulation of the number of transients to yield a sufficient signal to noise ratio (SNR) for obtaining a good image.

In general, in fact, the generation of a good substrate imaging in a reasonable time requires dealing with signal characterized by short $T_1$, in order to accumulate a high number of transients enhancing thereby the signal to noise ratio.

Nonetheless, the possibility of recording images of nuclei different from water protons appears highly attractive because the absence of signal from background is certainly very useful for improving the diagnostic content of the resulting MR image.

Moreover, there are a number of endogenous substances whose imaging would be extremely interesting and useful from the clinical point of view. A non-limiting list of such substances includes metabolites and substrates like lactate, citrate, carbonate, phosphate, pyruvate, natural amino-acids, oxalate, tartrate, succinate, choline, creatine, acetate, malonate. These molecules are involved in several human metabolic processes and changes in their normal production, as well as in their biodistribution, may be generally related to pathologic conditions.

Lactate, for example, is an endogenous metabolite of particular diagnostic relevance. It is an end product of the anaerobic glycolysis and, therefore, an increase of its concentration in tissues may be a clear indication of hypoxia, as it is found in some solid tumors. High levels of lactate are further present in conditions of reduced blood flow occurring in cerebral strokes or coronary infarcts or in presence of metabolic disorders or type I diabetes.

Another important metabolite, whose in vivo mapping would be very useful, is citrate. Its concentration in the case of prostatic tumor differs significantly between benign prostatic hyperplasia (BPH, high concentration) and malignant prostatic carcinoma (low concentration).

Hence, there remains a need for a Magnetic Resonance Imaging method which would allow the imaging of molecules different from water in a time suitable for a conventional medical practice and by conventional mode of operation.

SUMMARY OF THE INVENTION

It has now been found that a marked shortening of the relaxation times ($T_1$ and $T_2$) of the magnetic nuclei of a substrate molecule different from water can be obtained by exploiting a non covalent reversible binding between the substrate molecule and a suitable paramagnetic chelate complex.

In particular it has been found that the reversible binding between a substrate molecule and a suitable paramagnetic chelate complex allows the specific and selective high enhancement of the relaxation characteristics of the substrate nuclei of interest for the imaging procedure wherein this results in an easy and direct imaging of the substrate.

Quantitatively, the relaxation enhancement, $\epsilon$, of the substrate nuclei induced by the paramagnetic complex may be expressed in terms of this ratio:

$$\varepsilon = \frac{R_i^{s*}}{R_i^s}$$

in which $R_i^s$ represents the observed relaxation rate of the substrate nucleus of interest without paramagnetic promotion and $R_i^{s*}$ is the corresponding relaxation rate observed when the paramagnetic chelate is present in solution.

The relaxation rate $R_i$ is equal to $1/T_i$, wherein i=1 or 2.

A first object of the present invention is therefore a method for the Magnetic Resonance imaging of a substrate molecule different from water in a human or animal body organ or tissue characterised in that a paramagnetic chelate complex is employed which non covalently binds to the substrate molecule and as a result of said binding the relaxation enhancement ($\epsilon$) of the substrate nuclei of interest for the imaging procedure is at least 2 at 39° C. and pH 7.4.

The invention also refers to the use of a paramagnetic chelate complex or a physiologically tolerable salt thereof, said chelate complex being able to non covalently bind to the substrate molecule so that the relaxation enhancement ($\epsilon$) of the substrate nuclei of interest is at least 2 at 39° C. and pH 7.4, for the preparation of an enhancing agent for the magnetic resonance imaging of a substrate molecule different from water in a human or animal body organ or tissue.

Preferably, said relaxation enhancement is of at least 10 and, more preferably, is of at least 30 wherein said relaxation enhancement values are obtained independently from the applied magnetic field strength.

This non covalent binding between paramagnetic chelate complex and substrate molecule allows a marked shortening of the relaxation times ($T_1$ and $T_2$) of the magnetic nuclei of said substrate molecule allowing, in such a way, the acquisition of a particular high number of transients in a brief time and the registration of clear and diagnostically useful images in a short time, compatible with the clinical practice.

Moreover, by use of the paramagnetic complex according to the method of the invention, it is possible to obtain $^1H$ images of substrates in spite of the presence of the large signal arising from water. In this respect, in fact, when the substrate of interest interacts with a paramagnetic complex, according to this invention, the time required for the spectra acquisition is considerably shorter. Moreover, the water signal intensity is significantly reduced owing to the very rapid repetition time, and it can be further reduced by the use of a suitable pulse sequence.

Substrates molecules whose Magnetic Resonance Imaging is enhanced by the use of a suitable paramagnetic chelate complex according to the method of this invention include any molecule different from water which comprises one or more magnetic nuclei, i.e. nuclei with nuclear spin ≠0.

Said magnetic nuclei can also be in natural abundance in the substrate molecule or they can be "ad hoc" introduced or enriched in the substrate molecule of interest for the diagnostic procedure.

A non limiting example of substrate nuclei of interest for the imaging procedure includes $^1H$, $^{19}F$, $^{31}P$, $^{13}C$, $^{15}N$, wherein the substrate molecule is optionally labelled with $^{19}F$, $^{31}P$, $^{13}C$, $^{15}N$.

Preferably, said substrate molecule is an endogenous or an endogenously generated substrate, wherein the term "endogenous substrate" as used herein refers to a substrate which results from the normal or pathological behaviour of the biochemical process of cells and tissues and the term "endogenously generated substrate" as used herein refers to a substrate which results, in part or fully, from the transformation of a substance administered for the purpose of the diagnostic assay.

More preferably, the endogenous substrates are selected from the group consisting of lactate, citrate, carbonate, phosphate, pyruvate, natural amino-acids, oxalate, tartrate, succinate, choline, creatine, acetate, and malonate and the endogenously generated substrates are selected from the group consisting of lactate, citrate, carbonate, phosphate, pyruvate, natural amino-acids, oxalate, tartrate, succinate, choline, creatine, acetate and malonate generated in the body upon administration of suitably labelled precursors, such as $^{13}C$-enriched glucose, to metabolically yield $^{13}C$-enriched lactate.

Particularly preferred substrates are human metabolites, wherein lactate, citrate, carbonate or phosphate are the most preferred.

Moreover, the substrate molecule of the invention can be a non-endogenous substance, wherein the term "non-endogenous", as used herein, refers to any substance of pharmacological or diagnostic interest, optionally modified in order to allow a suitable binding to the paramagnetic complex and/or to introduce the magnetically active nuclei of interest for the imaging procedure.

Preferably, the non-endogenous substrate is selected from the group consisting of fluorinated or $^{13}C$- or $^{15}N$-labelled drugs, fluorinated or $^{13}C$- or $^{15}N$-labelled metabolites. Trifluoro-lactate, fluorinated citrate, $^{13}C$-labelled lactate, $^{13}C$-labelled citrate are particularly preferred.

When the substrate molecule to be imaged is non-endogenous, it may be administered to the patient as a sterile aqueous solution or suspension, optionally including a physiologically tolerable carrier.

It can be administered before the imaging, at the same time of the paramagnetic chelate complex. Optionally it can also be administered either before or after the administration of the paramagnetic complex.

To obtain the desired relaxation enhancement for the substrate nuclei, it is necessary that the $K_A$ of the adduct between the paramagnetic complex and the substrate molecule be at least $10\ M^{-1}$.

The $K_A$ constant, which expresses the thermodynamic stability of the adduct, is given by the usual equation $$ML + S \overset{K_A}{\leftrightarrow} (ML)(S)$$

$$K_A = \frac{[(ML)(S)]}{[ML][S]}$$

Since the relaxivity of the two paramagnetic species involved in the equilibrium, that bound to the substrate molecule and that unbound, are different, the well-established Proton Relaxation Enhancement (PRE) method (Aime S, Fasano M, Terreno E, Botta M in *The Chemistry of Contrast Agents in Medical Magnetic Resonance Imaging*, Merbach A E, Tóth E (eds), Wiley & Sons: Chichester, 2001, 203-209) may be conveniently used for estimating the affinity of the paramagnetic complex towards the substrate molecule.

The $K_A$ values obtained for the adducts disclosed in the following are measured according to this PRE method.

Moreover, the binding interaction between the substrate molecule and the paramagnetic chelate complex has to be kinetically labile in order to affect all the substrate molecules (S) in the presence of a limited amount of the paramagnetic chelate complex (ML)

Suitable kinetic lability is obtained when the residence lifetime of the substrate molecule bound to the paramagnetic complex, $\tau_M$, is $\leq T_{1M}$ (rapid exchange conditions).

Physiologically acceptable paramagnetic chelate complexes, in which the chelating ligand consists of a system which does not saturate the coordination number of the paramagnetic metal ion, are preferably used.

A further preferred class of physiologically acceptable paramagnetic complex according to the invention is represented by systems able to form a strong association with the substrate of interest, such as $LnDOTP^{4-}$ which can form tight ion-pairs with positively charged molecules.

Preferably, the chelating ligand comprises: a linear or cyclic polyaminopolycarboxylic, polyaminopolyphosphonic or polyaminopolyphosphinic acid residue or derivatives thereof including, for example, amide and ester derivatives as well as functional derivatives comprising suitable functional substituents on their structures; macrocyclic Shiff bases; porphyrins, or any ligand whose complex with a given paramagnetic metal ion is able to form a ternary complex with the substrate of interest. The paramagnetic ion is any lanthanide metal ion with an atomic number comprised from 58 to 70 or a transition metal ion with an atomic number from 21 to 29 and from 42 and 44. Preferably, the paramagnetic ion is selected from the group consisting of: gadolinium (III), iron (II), iron (III), manganese (II), manganese (III), chromium (III), cobalt (III), copper (II), nickel (II), dysprosium (III), erbium (III), terbium (III), holmium (III), thulium (III), ytterbium (III), europium (II) and europium (III). Gadolinium (III), manganese (II) and manganese (III) are particularly preferred.

Particularly preferred paramagnetic complexes for use in the method according to the invention are those in which the chelating ligand is selected from EDTA (ethylenediaminetetraacetic acid), PCTA (3,6,9,15-tetraazabicyclo[9.3.1]pentadeca-1(15)11,13-triene-3,6,9-triacetic acid), PCTP (3,6,9,15-tetraazabicyclo[9.3.1]pentadeca-1(15)11,13-triene-3,6,9-tris(methanephosphonic) acid), DOTP (1,4,7,10-tetraazacyclododecane-1,4,7,10-tetrakis(methanephosphonic) acid) and DO3A (1,4,7,10-tetraazacyclododecane-1,4,7-triacetic acid), including DO3A derivatives in which the non carboxylate nitrogen atom is suitably substituted with a pendant or a functional group.

A particularly preferred DO3A derivative is 10-[(3-methoxyphenyl)methyl]-1,4,7,10-tetraazaciclododecane-1,4,7-tris-[(aminocarbonyl)methyl]. The gadolinium complex thereof is herein referred to as Gd-1 complex.

Another preferred DO3A derivative is 10-[(3-methoxyphenyl)methyl]-1,4,7,10-tetraazaciclododecane-1,4,7-triacetic acid. The gadolinium complex thereof is herein referred to as Gd-2 complex.

A third preferred compound is 10-[(4-carboxyphenyl)methyl]-1,4,7,10-tetraazaciclododecane-1,4,7-triacetic acid, whose gadolinium complex thereof is herein referred to as Gd-3 complex.

All these ligands as well as their paramagnetic chelate complexes with gadolinium ion are new and are a further object of this invention.

The physiologically acceptable paramagnetic chelate complex may be employed in the form of salt thereof with suitable organic or inorganic acids or bases.

Preferred cations of inorganic bases include ions of alkali or alkaline-earth metals such as potassium, sodium, calcium, magnesium, and mixtures thereof.

Preferred cations of organic bases include those obtained by protonation of primary, secondary, and tertiary amines such as ethanolamine, diethanolamine, morpholine, glucamine, N-methylglucamine, and N,N-dimethylglucamine.

Anions of inorganic acids preferably include the ions of halo acids, i.e. chlorides, bromides, iodides or different ions such as the sulphate ion.

Anions of organic acids preferably include those used for salifying basic substances, such as acetate, succinate, fumarate, citrate and maleate.

Cations and anions of amino acids include, for example, taurine, glycine, lysine, arginine, ornithine, aspartic acid and glutamic acid.

The salifying cations and anions will obviously be selected so as not to interfere with the imaging procedure. In particular cations and anions corresponding to the substrate molecule to be imaged should be avoided.

The paramagnetic complex for use in the method according to this invention may be represented by a single molecule or it may optionally be administered under the form of covalent or non-covalent aggregates of different size.

For instance, it may be bound to a molecule endowed with specific pharmacological or diagnostic properties or it may be covalently or non-covalently bound to a protein, to a polyaminoacid, to a macromolecular substrate. Analogously, upon introducing suitable functionalisations on the surface of the chelate, it may form supramolecular adducts with other molecules, proteins, polyaminoacids or macromolecular systems.

Moreover, the paramagnetic complex or a suitable aggregate thereof can optionally be conjugated to a suitable moiety responsible for its targeting to the desired body region, tissue or organ. A non limiting example of suitable moieties includes peptides and fragments thereof and targeting receptors over-expressed in the presence of pathological conditions.

Further, the paramagnetic complex can optionally be inglobated into liposomes, vesicles or other suitable carriers.

The ultimate choice of the paramagnetic metal complex suitable for the claimed use and method will depend on several properties including the electric charge and the solution structure of both the metal complex and the substrate, the concentration of the interacting partners in the tissue or organ to be imaged, the instrumental conditions of the intended analysis. The skilled practitioner will be anyhow able to select a suitable complex by merely applying routine methods, as detailed in the Examples. In particular, a first selection will be made by taking into account the structural features of the intended substrate, particularly its electric charge, the donor ability of its chelating moieties (e.g. carboxy-, hydroxy-, amino-, phosphonate, thio-, sulfonate groups etc.) and its overall steric hindrance. A paramagnetic metal complex matching said structural features of the substrate can usually be selected out from the known classes of paramagnetic metal complexes, for example from complexes of linear or cyclic polyaminopolycarboxylic, polyaminopolyphosphonic or polyaminopolyphosphinic ligands such as EDTA, PCTA, PCTP, DOTP and DO3A. If necessary, the ligand core may be modified by inserting suitable functional groups expected to improve the non-covalent binding and/or increase the exchange rate between the free- and the metal complex bound-form of the substrate (e.g. by means of hydrogen bonds or by exploiting other ionic and/or hydrophobic interactions). The determination of the relaxation enhancement $\epsilon$ and of the affinity constant $K_A$ is then carried out, to confirm the theoretical expectations made in the selection phase.

The paramagnetic complex used in the method according to the invention can suitably be formulated as sterile aqueous solutions or suspensions, whose pH can range from 6.0 to 8.5, either alone or optionally with other physiologically acceptable ingredients. The pharmaceutical preparations can be suitably injected intravasally (for instance intravenously, intraarterially, intraventricularly, and so on) or used by way of intrathecal, intraperitoneal, intralymphatic, intracavital, oral or enteral administration.

These aqueous solutions or suspensions are stable and can be formulated as such or they can formulated as a lyophilisate and reconstituted just before use. They can be administered in a concentration ranging between 0.0001 and 1.0 M.

The paramagnetic chelate complex is administered early enough before the MRI monitoring to allow for the distribution of the agent to the body organ or tissue to be imaged.

The method of the invention includes the steps of generating a magnetic field around the human or animal body, body organ or tissue of interest by use of a large magnet which forces the magnetic nuclei possessing a magnetic moment $\neq 0$ of said human or animal body, body organ or tissue to align themselves with the field direction, applying radio pulses of suitably selected frequency which move said magnetic nuclei out of alignment, and collecting the radiofrequency emitted when the same come back into equilibrium conditions containing spatial and intensity information and processing them by a suitable computer to produce the body organ or tissue desired image.

The magnitude of the applied magnetic field is at least 60.000 times more intense than the Earth's one but it is not substantially greater than 3 Tesla for in vivo imaging, while it could be even higher for the ex vivo samples. The frequency of the applied radio pulses is suitably selected according to the precession frequency of the magnetic nuclei of interest for the imaging procedure. The selection of a proper pulse frequency allows, for example, the direct $^{13}C$ observation and the direct imaging based on these observations.

When $^1H$-image are desired, the fully exploitation of the imaging method of the invention is preferably based, even if not limited to, on the possibility to record an inverse-detected image. Through this experimental modality, it is possible, by the use of a proper pulse sequence, to obtain an $^1H$-image collecting the signal only from the protons bound to $^{13}C$ nuclei. This procedure still results in an image without background signals, as in the case of a direct $^{13}C$ observation, but with a great sensitivity enhancement due to the observation of a considerably more sensitive nucleus.

$^1H$-images can also be obtained exploiting different experimental modality such as, for example, the MRSI imaging technique which can be advantageously used even if the concentration of the substrate molecule is not abundant and which does not request the concomitant presence of a suitably labelled substrate.

The Magnetic Resonance Imaging is an imaging procedure available only since 1980. This technology is however well known to those skilled in the art and will not be detailed here. Quite important, anyway, is to point out that the imager can operate in various modes depending on, for example, the exciting radio frequency selected pulses, which may be varied according to the information sought from the organ or tissue under examination, as well as the MR imaging parameters adopted. All these can be selected, within a given limit, by the operator, optionally on the basis of available protocols, resulting in flexibility.

A further object of the invention is a pharmaceutical composition comprising a paramagnetic chelate complex or a physiologically acceptable salt thereof, together with a physiologically tolerable carrier, wherein the paramagnetic chelate complex non covalently binds to the substrate molecule, thereby enhancing the relaxation of the substrate nuclei at least 2 at 39° C. and pH 7.4.

The pharmaceutical compositions can also optionally comprise a non-endogenous substrate molecule, such as a substrate molecule artificially enriched in or labelled with a particular substrate nucleus or isotope, or a suitable pro-drug of the same, which transforms into the suitable diagnostically active form upon time, by action of agents such as enzymes, oxidants, reductants, acids, bases or ions.

The invention moreover concerns a pharmaceutical composition comprising a non-endogenous substrate molecule such as a molecule artificially enriched in or labelled with a particular substrate nucleus or isotope, or a suitable pro-drug of the same, together with a physiologically tolerable carrier, which can advantageously be employed, for example, when the suitable paramagnetic chelate complex and the non-endogenous substrate molecule need to be administered at different times.

The pharmaceutical compositions can be administered either intravascularly, i.e. intravenously, intraarterially, intracoronarically, or used by way of intrathecal, intraperitoneal, intracavital, enteral or oral administration.

When the substrate molecule to be imaged is non-endogenous, it may be administered to the patient before the imaging, at the same time of the paramagnetic chelate complex or, optionally, either before or after its administration.

A further object of the invention is a therefore kit for use in a method of the invention which comprises a first pharmaceutical composition including a non-endogenous substrate molecule, or a pro-drug thereof, together with a physiologically tolerable carrier, and a second pharmaceutical composition which includes a physiologically acceptable paramagnetic chelate complex or a salt thereof, together with a physiologically tolerable carrier, wherein said non-endogenous substrate molecule and said paramagnetic chelate complex are suitably selected so that the paramagnetic chelate complex non covalently binds to the non-endogenous substrate and as a result of said binding the relaxation enhancement (ε) of the substrate nuclei of interest for the imaging procedure is at least 2 at 39° C. and pH 7.4.

Preferred non-endogenous substrates for the kits of the invention are: trifluoro-lactate, fluorinated citrate, $^{13}$C-labelled lactate, $^{13}$C-labelled citrate.

These kits allow the selection of the most suitable non-endogenous substrate, providing the best visualization of the body organ or tissue of interest, while allowing the best choice of the timing of injection of the paramagnetic complex versus the substrate molecule.

Figure 1:
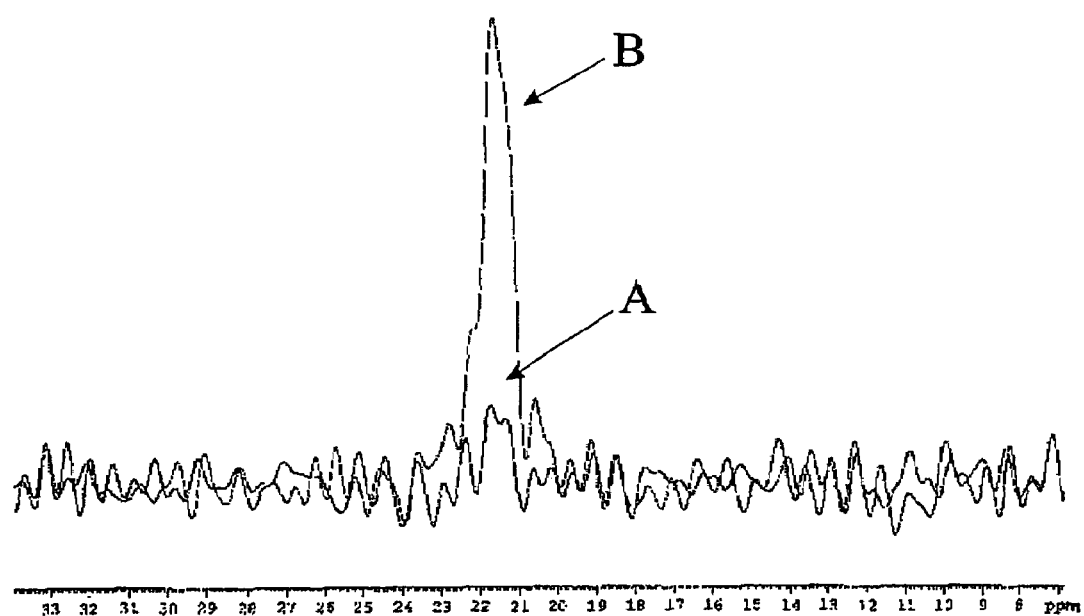
FIG. 1: $^{13}$C-NMR Spin-Echo spectra of a solution of lactate (10 mM, 50% 13C-enriched at the methyl position) with (trace B) and without (trace A) GdDO3A 1 mM. Acquisition conditions: 7.1 T, 312K, solution pH 7.

All the five capillaries contain a 20 mM solution of inorganic phosphate (pH 7.4) and different concentrations of GdDO3A. A=no GdDO3A, B=0.25 mM, C=0.5

Imaging of Lactate

As a non limiting example of the wide range of applications of the present invention, the enhancement of the relaxation rates of lactate, and therefore of its signal in a MR image, by the use of a paramagnetic complex is reported hereinafter.

As previously pointed out, lactate is an endogenous metabolite, which is produced at increased rate whenever glycolysis accelerates. Its presence and accumulation in some body organs or tissue changes during pathological activation and generally indicates the presence of a pathologic state.

Under normal conditions, for example, lactate is not detected in the brain. Its presence indicates that the normal oxidative respiration at the cellular level has been altered and that carbohydrates are being catabolised by an anaerobic pathway. This situation occurs in several cellular and metabolic lesions that are thought to outgrow their blood supply. The presence of lactate may therefore indicate a high degree of malignancy. As such this metabolite is found in multiform glyoblastoma.

An increase of the lactate level is also caused by acute brain infarction and stroke.

The imaging of this substrate, enhanced by the use of a paramagnetic complex according to the invention, surely provides a powerful aid in the clinical investigation of the related pathologies.

Being lactate a bidentate ligand, good binding is reasonably obtainable when two coordination vacancies at the metal centre of the paramagnetic complex are available. Lactate coordinates through two oxygen donor atoms and therefore Gd(III) ion, which is an "hard" ion, is well suitable. In order to prevent problems associated with the release of toxic Gd(III) ions, the metal ion has to be administered under suitable forms. Among several possibilities the neutral complex formed by Gd(III) and the ligand DO3A (1,4,7,10-tetraazacyclododecane-1,4,7-triacetic acid) represents a good choice to illustrate the purpose of this invention. In fact, DO3A is an heptadentate ligand based on a tetraazacyclododecane ring in which only three nitrogens bear a coordinating acetic arm. The coordination number of Gd(III) ion with this ligand is nine, so the two vacancies in GdDO3A are occupied by two water molecules. The formation constant of GdDO3A is ca $10^{21}$, i.e. a very safe value for "in vivo" applications.

By adding lactate to an aqueous solution of GdDO3A the following equilibrium takes place:

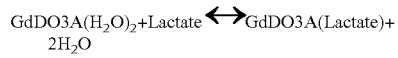

$$\text{GdDO3A(H}_2\text{O)}_2 + \text{Lactate} \leftrightarrow \text{GdDO3A(Lactate)} + 2\text{H}_2\text{O}$$

Since the relaxivity of the two Gd(III) species involved in the equilibrium are different (higher for GdDO3A(H$_2$O)$_2$), the well-consolidated Proton Relaxation Enhancement (PRE) method (Aime S, Fasano M, Terreno E, Botta M in *The Chemistry of Contrast Agents in Medical Magnetic Resonance Imaging*, Merbach A E, Tóth E (eds), Wiley & Sons: Chichester, 2001, 203-209) may be conveniently used for estimating the affinity of the GdDO3A complex towards Lactate.

On this basis, a K$_A$ value of 150 M$^{-1}$ at pH 7 and 25° C. has been determined. Then, in a solution containing 10 mM of Lactate and 1 mM of GdDO3A, the ratio [Lac]$_{bound}$/[Lac]$_{total}$ is $5.8 \cdot 10^{-2}$, i.e. more than three order of magnitude higher than the value of the [H$_2$O]$_{bound}$/[H$_2$O]$_{total}$ ratio in the experiment dealing with water protons and carried out with the same concentration of GdDO3A.

The condition of fast exchange between free and bound Lactate has been verified.

The reversible interaction of lactate at the paramagnetic Gd(III) centre promotes a dramatic reduction of T$_1$ and T$_2$ of its resonances. In fact, in the solution containing GdDO3A 1 mM and Lactate 10 mM, the T$_1$ (at 7.05 T and 39° C.) of the $^1$H-methyl resonance passes from 2.9 s to 8.0 ms, whereas in an analogous experiment T$_1$ of the $^{13}$C-methyl resonance passes from 3.5 s to 30.0 ms wherein the relaxation enhancement for $^1$H-methyl, $^{1H}$ε is 362.5 while $^{13C}$ε is 116.7.

FIG. 1 shows the $^{13}$C NMR spectrum ($^1$H-decoupled) of 10 mM of Lactate, 50% $^{13}$C-enriched at the methyl group, in the absence (trace A) and in the presence (trace B) of GdDO3A 1 mM.

At 7.05 T and 25° C., we carried out the acquisition of 1 k transients in 1'17" through a conventional T$_1$-weighted spin-echo (SE) sequence. The long T$_1$ of the $^{13}$C-methyl resonance of Lactate does not allow the clear detection of any signal in the absence of paramagnetic complex. On the contrary, when the same experiment is repeated in the presence of GdDO3A a relatively intense signal comes out.

Besides the direct $^{13}$C observation, an alternative approach for fully exploiting the marked relaxation enhancement of the $^1$H and $^{13}$C-lactate resonances in the presence of a paramagnetic relaxation agent is based on the possibility to record an inverse-detected image. Through this experimental modality, it is possible, by the use of a proper pulse sequence, to obtain an $^1$H-image collecting the signal only from the protons bound to $^{13}$C nuclei. This procedure still results in an image without background signals, as in the case of a direct $^{13}C$ observation, but with a great sensitivity enhancement due to the observation of a considerably more sensitive nucleus. Moreover, a further shortening of the acquisition time for obtaining the image results from the fact that the acquired signal is dependent on the $^1H$ relaxation times, which are significantly shorter than those ones of the coupled $^{13}C$ nuclear spin.

A $T_1$-weighted image, based on a HMQC pulse sequence inserted before the conventional gradient echo (GE) pulse sequence, has been recorded on a high resolution spectrometer endowed with a 5 mm micro-imaging probe, operating at 11.75 T.

The HMQC (Heteronuclear Multiple Quantum Coherence) pulse sequence provides correlation between protons and their attached heteronuclei ($^{13}C$ in this case) through the heteronuclear scalar coupling. This sequence is very sensitive as it is based on proton detection instead of the detection of the least sensitive low gamma heteronuclei.

Figure 2:
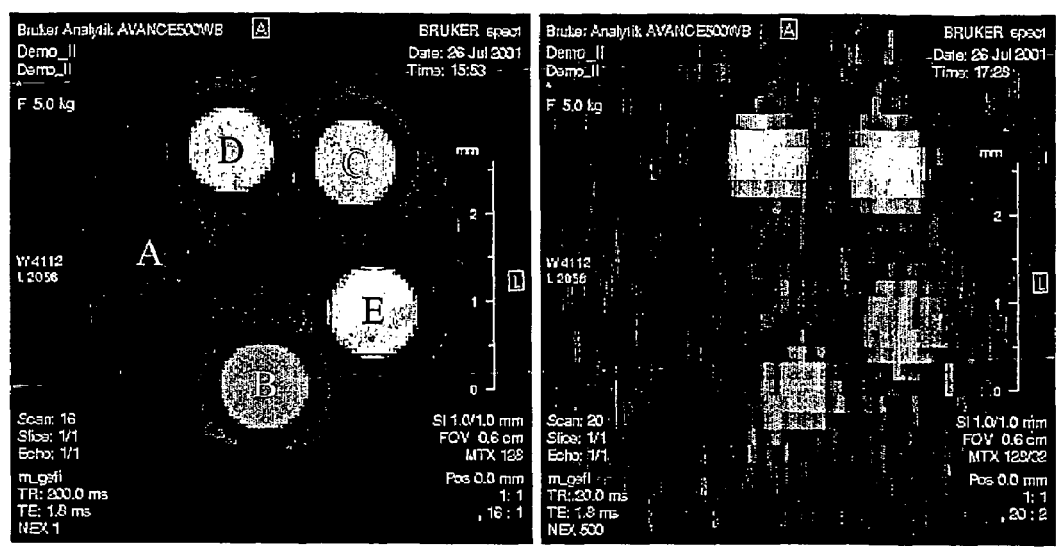
FIG. 2: MRI images recorded at 11.75 T on a 5 mm microimaging probe. Left: $^1$H-MRI of water obtained by means of a conventional GE pulse sequence. All the capillaries contain 10 mM of lactate 100% $^{13}$C-enriched at the methyl position and different concentrations of GdDO3A (pH of the solutions=7). A=no GdDO3A, B=0.25 nM, C=0.5 mM, D=1 mM, E=2 mM. Right: $^1$H-MRI "inverse-detected" of lactate of the same phantom obtained by means of a pulse sequence consisting of a HMQC-like pulse sequence followed by a GE sequence.

The result is reported in FIG. 2 (right). On the left, a conventional $^1H$-image is shown reporting the signal from water protons in order to localise the different samples. The phantom was formed by 5 capillaries (diameter about 1 mm) inside a 5 mm NMR tube containing water. The samples consisted of aqueous solutions of Lactate 10 mM (100% $^{13}C$ enriched at the methyl group) with different concentrations of GdDO3A (A=no GdDO3A, B=0.25 mM, C=0.5 mM, D=1 mM, and E=2 mM).

The inverse-detected image was obtained in 5'20" by collecting 512 transients with a repetition time (TR) of 20 ms and an echo-time (TE) of 1.8 ms. Whereas no signal is detected for the sample A, there is enough signal intensity in the other samples. Interestingly, sample E, which contains the highest amount of GdDO3A shows less signal than C and D. This is a consequence of $T_2$-effects due to the very short $T_2$ relaxation time of the $^1H$-methyl lactate signal in the presence of relatively high concentration of the paramagnetic relaxation agent. In other words, higher GdDO3A concentrations, by keeping fixed the total amount of lactate, lead to an increase of the $[Lac]_{bound}/[Lac]_{total}$ ratio, thus, reducing both $T_1$ and $T_2$ of the $^1H$-methyl resonance. On this basis, the relatively weak signal emerging from sample E is the result of the broadening of the resonance. The signal detected for sample B, which contains the lowest GdDO3A concentration, is quite similar to sample E, but now this is due to the relatively long $T_1$ of the $^1H$-methyl resonance of lactate in the presence of a small amount of the relaxation agent. This is an interesting result because it means that the maximum contrast to noise ratio (CNR) is achieved at relatively low concentration of GdDO3A.

As mentioned above, an object of this invention is the use of a paramagnetic complex to obtain images of non-endogenous substrates.

As a non limiting example for illustrating this further aspect of this invention we used Trifluoro-lactate as imaged substrate.

$^{19}F$ has a nuclear spin of ½ and a natural abundance of 100%.

At 7.05 T and 312° K, the relaxation time $T_1$ of $^{19}F$ resonance of a 10 mM solution of $CF_3$—$CH(OH)$—$COO^-$ is 4.5 s.

Upon the addition of GdDO3A 0.9 mM the $T_1$ value becomes 23.0 ms wherein the relaxation enhancement $^{19F}\epsilon$ is 195.6.

Figure 3:
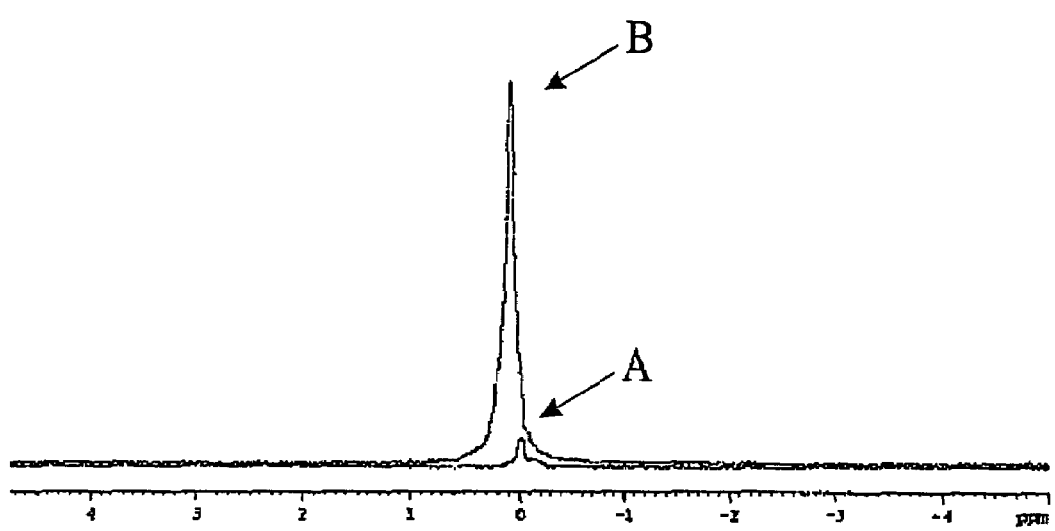
FIG. 3: $^{19}$F-NMR Spin-Echo spectra of a 10 mM solution of trifluoro-lactate with (trace B, 0.9 mM) and without (trace A) GdDO3A (acquisition conditions: 7.1 T, 312K, pH 7).

FIG. 3 shows the $^{19}F$-NMR spectra ($T_1$-weighted SE sequence) of these two aqueous solutions (trace A=no GdDO3A).

The observed enhancement promoted by the interaction with the paramagnetic substrate is even higher than the one previously shown in FIG. 1 for the $^{13}C$-methyl resonance, either because of the higher γ-value for $^{19}F$ nuclear spin or for the presence of three equivalent $^{19}F$ nuclei in each trifluoro methyl moiety.

Figure 4:
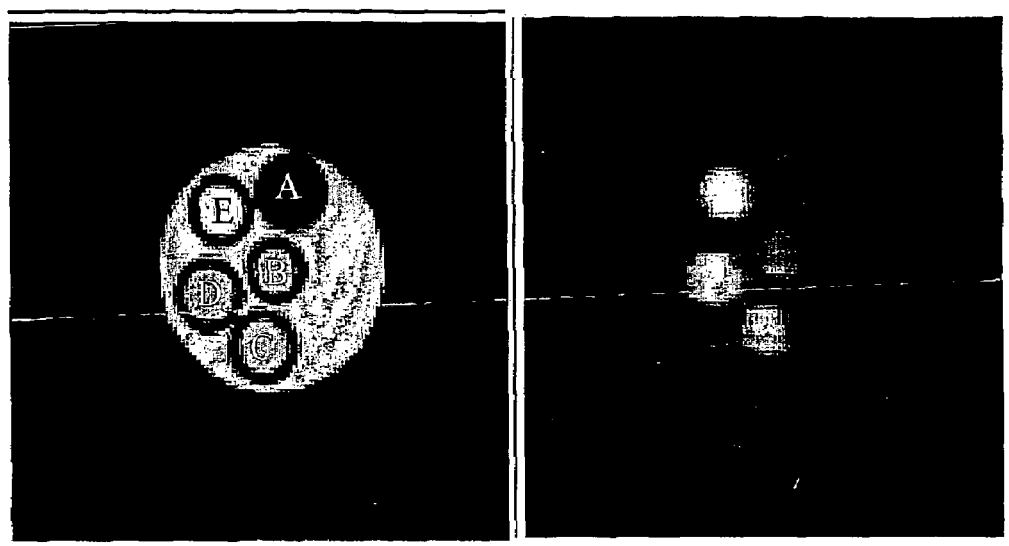
FIG. 4: MRI images recorded at 7.1 T on a 5 mm microimaging probe. Left: $^1$H-MRI of water obtained by means of a conventional GE pulse sequence. All the capillaries contain 10 mM of trifluoro-lactate (pH 7) and different concentrations of GdDO3A. A=no GdDO3A, B=0.25 mM, C=0.5 mM, D=1 mM, E=2 mM. The solution outside the five capillaries is represented by water doped with CuSO$_4$. Right: $^{19}$F-MRI of trifluoro-lactate of the same phantom obtained by means of a conventional GE sequence.

FIG. 4 (right) shows a $^{19}F$ image of trifluoro-lactate obtained at 7.1 T on a 5 mm micro-imaging probe. On the left in the same figure it is also reported a conventional GE image for water protons. All the five capillaries (about 1 mm diameter) contain a 10 mM solution of the non endogenous substrate trifluoro-lactate and different concentrations of the relaxation agent GdDO3A (A=no GdDO3A, B=0.25 mM, C=0.5 mM, D=1 mM, and E=2 mM). The capillaries have been introduced into a 5 mm NMR tube containing water doped with copper(II) sulfate. The left image allows the identification of the different samples. The right image ($^{19}F$) was obtained with a conventional GE sequence (TR=20 ms, TE=1.1 ms) in 5'15" through the acquisition of 512 transients. In this case the best CNR value corresponds to the sample E, which contains the highest concentration of GdDO3A, but a relatively good contrast is still observable for sample B, whereas no signal is detected in the sample without the paramagnetic complex.

A marked increase of the relaxation enhancement of $^{19}F$ nuclei in Trifluoro-lactate may be obtained by using a Gd(III) complex able to stronger interact with the non-endogenous substrate. Gd-2 complex has a $K_A$ value with Trifluoro-lactate of 60 at 298 K, i.e. about 6 times larger than GdDO3A.

For this reason a $T_1$ value of 11.8 ms and a relaxation enhancement of 381.3 has been measured at 312 K for the $^{19}F$ nuclei of the substrate (10 mM) in a 0.9 mM solution of Gd-2.

The Citrate Issue

In addition to the enhanced imaging reporting the lactate distribution, the present invention further allows an advantageous visualization of citrate in human body tissues, mainly addressed to the prostate gland.

As discussed before, the citrate concentration in the normal prostate gland differs significantly from corresponding concentration in benign prostatic hyperplasia (BPH) and in malignant prostatic carcinoma. Prostate cancer is now the most commonly occurring malignancy in man, exceeding even lung cancer, and it represents the second biggest cause of cancer-related death.

The enhanced imaging of the citrate molecule obtained according to this invention will allow the mapping of the distribution and concentration of this metabolite in the prostatic tissue and, consequently, will lead to the differentiation between the prostatic carcinoma and the benign pathology, without need of surgical biopsies which are invasive and traumatic for the patient.

Chemically, citrate is an hydroxy-tricarboxylic acid and, in principle, it may bind the paramagnetic complex with different modalities. Nevertheless, citrate binds GdDO3A weaker than lactate ($K_A$ of 40 $M^{-1}$ at pH 7 and 25° C.). It is likely that citrate may interact with GdDO3A mainly through the carboxylate and the hydroxy group in position 3, similarly to lactate, but here the two acetate groups of citrate could represent a steric hindrance for the binding.

An enhanced affinity towards citrate is shown by a derivative of GdDO3A, the gadolinium complex of the 10-[(3-methoxyphenyl)methyl]-1,4,7,10-tetraazaciclododecane-1,4,7-tris-[(aminocarbonyl)methyl] chelating ligand, in which the three carboxylic groups have been transformed into carboxamide groups, and the fourth nitrogen atom of the macrocyclic ring (N—H in GdDO3A) has been substituted with a 3-(methoxyphenyl)methyl substituent. The resulting three-positively charged paramagnetic chelate Gd-1 binds citrate very strongly, with a $K_A$ value $\geqq 20000$ $M^{-1}$ at pH 7 and 25° C.

The large difference in the affinity towards citrate between GdDO3A and Gd-1 is ascribed to the different electric charge and, likely to a smaller extent, to the presence of the non coordinating substituent on the nitrogen of the macrocyclic ring. In fact, we observed that the introduction of a pendant substituent in such position may enhance the binding between the substrate and the paramagnetic GdDO3A derivative.

The ternary complex [Gd-1(citrate)] deriving from the interaction of a citrate with Gd-1 complex is new and is a further object of this invention Other Substrates The use of a paramagnetic complex according to the present invention further allows the enhanced imaging of a number of substrates. A non-limiting list includes alanine, a non-essential amino acid which has been found to be present at high concentration in some meningiomas, choline, one of the most important metabolite the presence and concentration of which increases in primary and secondary brain tumors; creatine and phosphocreatine, which are involved in the production of adenosine-triphosphate and are present at decreased concentration in several brain tumors; N-acetyl aspartate, an intracellular metabolite whose detection may provide information on the neuronal loss; inorganic phosphate and phosphorylated metabolites, which are involved in the energetic metabolic processes.

For the latter substrates, GdDO3A represents again a good candidate as relaxation agent. The binding strength between GdDO3A and inorganic phosphate is 50 $M^{-1}$ at pH 7.4 and 25° C., and the substrate acts as monodentate towards the paramagnetic complex. This means that one residual water molecule is still present in the inner coordination sphere of the Gd(III) ion in the ternary complex.

$^{31}P$ has a nuclear spin of ½, a natural abundance of 100%, but a γ-value smaller than $^1H$ and $^{19}F$.

The $T_1$ of a 20 mM solution of inorganic phosphate at 7.1 T, pH 7.4, and 39° C. is very long (about 10 s), but in the presence of 0.2 mM of GdDO3A it dramatically shortens to 36 ms ($^{31P}\epsilon$=277.8). The very short $T_1$ of $^{31}P$-phosphate, with respect $^1H$-, $^{13}C$-, and $^{19}F$-lactate, is due to the closer proximity of the $^{31}P$ nucleus to the metal centre in the ternary complex.

Figure 5:
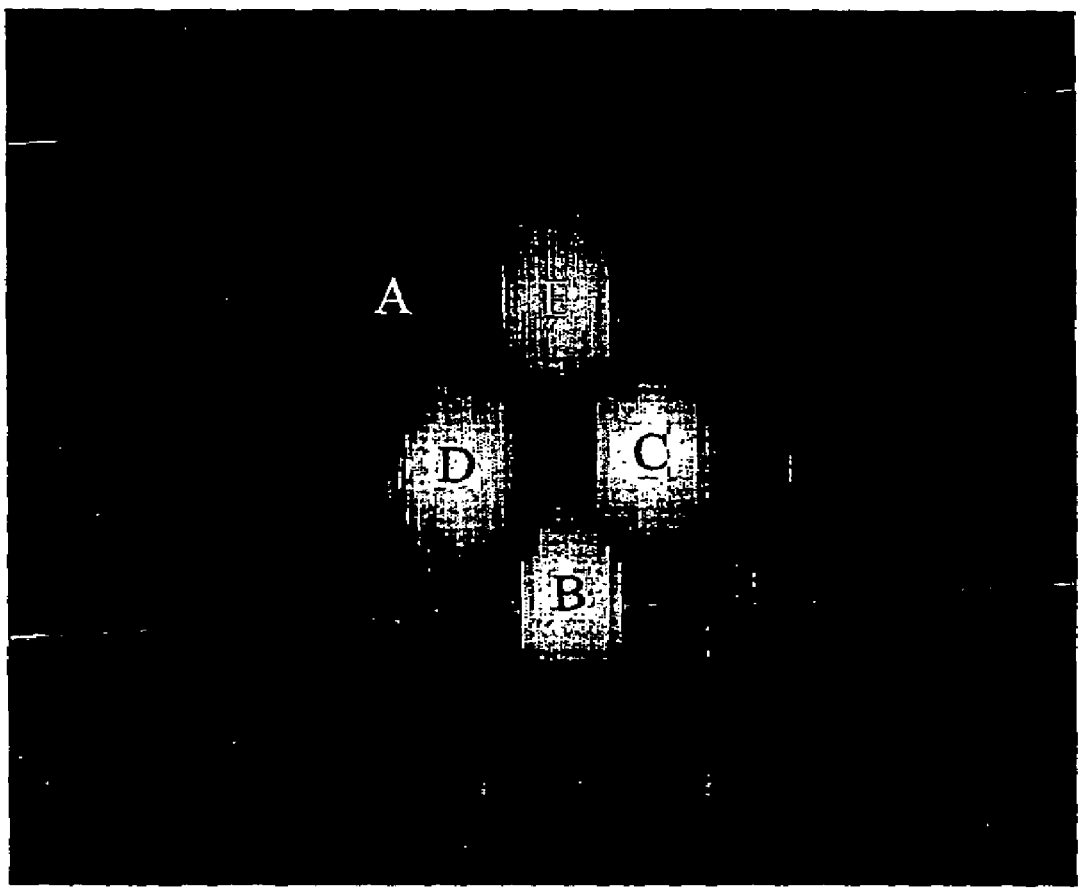
FIG. 5: $^{31}$P-MRI SE image recorded at 11.75 T on a 5 mm micro-imaging probe.

FIG. 5 $^{31}P$ shows images of inorganic phosphate 20 mM in the presence of different concentrations of GdDO3A. The images were obtained on a 5 mm micro-imaging probe at 11.75 T by using a conventional SE sequence (1 hour of acquisition time, TR=13 ms, TE=1.5 ms, 10000 transients acquired).

The phantom consists of five 1 mm capillaries introduced in a 5 mm NMR tube containing water. The GdDO3A concentration inside the capillaries is: 0 (sample A), 0.25 mM (sample B), 0.5 mM (sample C), 1 mM (sample D) and 2 mM (sample E). In analogy with the image shown in FIG. 2, the best CNR is not observed in the sample with the highest GdDO3A concentration, owing to $T_2$ effects.

Other examples dealing with the recognition ability of Gd(III) complexes toward substrates of biological relevance include Gd-2 and tartrate ($K_A$ of 3000 at 298 K and pH 7), Gd-3 and oxalate (very high affinity, $K_A$>50000 at 298K and pH 7) and Gd-3 and aspartate ($K_A$ of 120 at 298 K and pH 7).

In addition to the enhanced imaging of metabolites of particular clinical interest exemplified so far, the method of the invention further allows the visualisation of substances of different nature and biological function, such as antigens and receptors.

In a further aspect, the present invention also relates to the targeting and the enhanced visualization of a human or animal organ or tissue component and, particularly, of an antigen or a receptor, by use, in the method of the invention, of a suitable paramagnetic chelate complex which non covalently binds to a substrate molecule according to said method and, further, is conjugated to or functionalized with a suitable targeting vector well recognised by the organ or tissue component of interest in the imaging procedure.

In particular, the use in the method of the invention of a pharmaceutical composition including this targeted paramagnetic complex allows the enhanced visualisation of membrane receptors, such as PSMA, a cellular membrane receptor of the prostate cells; EGF, which is the endothelial grown factor responsible for the development of the microvascularized system in malignant tumors; or MUC1, a membrane receptor whose glycosylation degree changes in the presence of some tumors and malignancies.

The imaging of such membrane receptors can be practically obtained by administration to the patient of a pharmaceutical composition for use in the method of the invention including, for instance, GdDO3A complex, and preferably a polymer containing a number of GdDO3A or GdDO3A derivative units, conjugated to or functionalized with a suitable targeting vector selected among a polypeptide, an antibody or a suitable Fab, which are well recognised by the receptor of interest, and which binds to it.

Alternatively, the accumulation of GdDO3A may be pursued through the set-up of non covalent supramolecular adducts. Moreover, one may pursue the visualisation of the cells bearing the receptor of interest through the internalisation of a high number of paramagnetic agents.

About 24 hours after the administration of this pharmaceutical composition, $^{13}C$-enriched Lactate or trifluoro-lactate is administered to the patient under examination. The labelled lactate uniformly distributes in the body organs and tissues and exchanges with the endogenous lactate. When the organ or tissue of interest is imaged, only the $^1H$-, $^{13}C$-coupled, methyl lactate resonance or the $^{19}F$ resonance of trifluoro-lactate, bound to the GdDO3A complex targeted to the membrane cell may be detected in a short time, allowing the target visualisation.

In addition, a GdDO3A-like complex, suitably functionalised with the polypeptide or the antibody able to target the complex to the membrane receptor of interest, is administered to a patient. Because of the presence of the targeting moiety, the GdDO3A complex derivative is internalised into the targeted cells.

$^{13}C$-methyl enriched lactate or trifluorolactate is then administered to the patient and it distributes in the body organs and tissues. When the inverse detected $^1H/^{13}C$ image (or direct $^{19}F$ image) of the body region of interest is acquired, the recovered signal only derives from the labelled lactate molecules internalised into the targeted cells. The short $T_1$ of the nucleus examined, caused by the lactate-paramagnetic complex interaction, allows the collection of a huge number of transients in a short time, thus enhancing the SNR.

EXPERIMENTAL SECTION a) Preparation of 10-[(3-methoxyphenyl)methyl]-1,4,7,10-tetraazaciclododecane-1,4,7-tris-[(aminocarbonyl)methyl]gadolinium complex (Gd-1 complex) of formula:

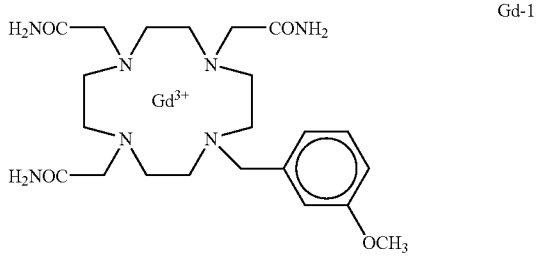

The chelating ligand was synthesised according to the following steps:
- a. 1,4,7,10-tetraazacyclododecane (TAZA) was N-alkylated by reaction with 3-(methoxyphenyl)methyl bromide in a 5:1 ratio (solvent acetonitrile/water 1:1, room temperature);
- b. acetonitrile was, removed and the remaining aqueous solution was extracted with ethyl acetate. The organic fractions were evaporated giving a product (pale yellow oil) containing both the mono- and the bis-alkylated TAZA derivatives.
- c. bromo-acetamide was added to the intermediate of step b) in dry acetonitrile in the presence of $K_2CO_3$ as base and the resulting solution was refluxed for 30'. The mono-alkyated ligand was obtained from the reaction mixture as white solid by filtration.

b) Preparation of 10-[(3-methoxyphenyl)methyl]-1,4,7,10-tetraazaciclododecane-1,4,7-triacetic acid gadolinium complex (Gd-2 complex) of formula:

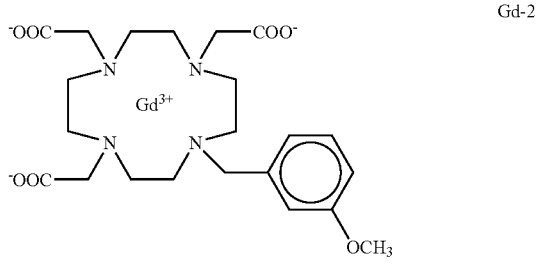

The synthesis of this chelating ligand was carried out by starting from the intermediate of step b) (synthesis of ligand 1). Bromoacetic acid was added to this product (molar ratio 4:1) and the pH of the solution was brought up to 10 by adding NaOH 10 N. After heating (50-60° C.) for 6 hours the solution was filtered and acidified with HCl 10% up to pH 2.5. The final product was purified by liquid cromatography. A first eluition was carried out by using Amberlite® XAD 1600 (eluent: gradient of methanol up to 40% in water) in order to separate the product from the bis-alkylated TAZA derivatives. Then, a second eluition was performed by using Duolite® C20 MB (eluent: $NH_4OH$ 2.5 M) in order to separate the ligand 2 from salts and from the excess of Bromoacetic acid.

c) Preparation of 10-[(3-carboxyphenyl)methyl]-1,4,7,10-tetraazaciclododecane-1,4,7-triacetic acid gadolinium complex (Gd-3 complex) of formula:

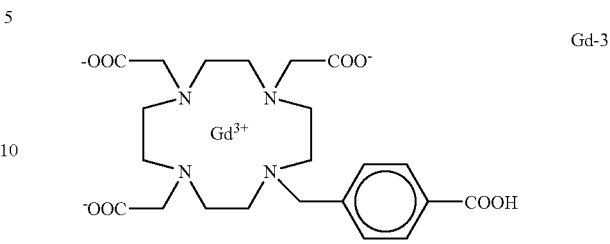

The chelating ligand was synthesised according to the following steps:
- a) 1,4,7,10-tetraazacyclododecane (TAZA) was N-alkylated by reaction with 3-(carboxyphenyl)methyl bromide in a 5:1 ratio (solvent water, room temperature, overnight);
- b) The pH was brought to 7 by adding HCl and the solution was concentrated. The alkylated products are extracted with absolute ethanol and the resulting solution is evaporated to dryness. The solid was dissolved in water and the alkylated products are separated by cationic-exchange cromatography (eluent: $NH_4OH$ 2N).
- c) Bromoacetic acid was added to the alkylated products product (molar ratio 4:1) and the pH of the solution was brought up to 10 by adding NaOH 10 N. After heating (50-60° C.) for 6 hours the solution was filtered and acidified with HCl 10% up to pH 2.5. The final product was purified by liquid cromatography. A first eluition was carried out by using Amberlite® XAD 1600 (eluent: gradient of methanol up to 40% in water) in order to separate the product from the bis-alkylated TAZA derivatives. Then, a second eluition was performed by using Duolite® C20 MB (eluent: $NH_4OH$ 2.5 M) in order to separate the ligand 2 from salts and from the excess of Bromoacetic acid.

All the Gd(III) complexes were prepared in water (room temperature, pH 7-8) by addition of Gd(III) chloride to an aqueous solution of the given ligand in stoichiometric ratio 1:1. After reaction, the solution was filtered (Millipore®), concentrated and desalted through a Dowex® column to give the title complex compound.

The invention claimed is:
1. A method of obtaining images comprising:
administering a paramagnetic chelate complex comprising a lanthanide metal ion with atomic number ranging from 58 to 70, or a transition metal ion with atomic number from 21 to 29 and from 42 and 44 and a chelating ligand selected from, 10-[(3-methoxyphenyl)methyl]-1,4,7,10-tetraazaciclododecane-1,4,7-tris-[(aminocarbonyl)methyl], and 10-[(3-methoxyphenyl)methyl]-1,4,7,10-tetraazaciclododecane-1,4,7-triacetic acid, or a physiologically acceptable salt thereof, which non covalently binds with a binding strength of at least 10M-1 to a substrate molecule, thereby shortening the relaxation times of the magnetic nuclei of the substrate molecule by forming a non-covalent reversible binding between the substrate and the paramagnetic chelate complex and
registering the image of the substrate molecule in a human or animal body organ or tissue by use of the Magnetic Resonance Imaging techniques,
wherein said image is obtained in vivo and wherein said substrate molecule is an endogenous substrate selected from lactate, citrate, carbonate, phosphate, pyruvate, natural amino-acids, oxalate, tartrate, succinate, choline, creatine, acetate, and malonate in a human or animal body organ or tissue.

2. The method of claim 1 for the Magnetic Resonance Imaging of lactate, wherein said paramagnetic chelate complex is 10-[(3-methoxyphenyl)methyl]-1,4,7,10-tetraazaciclododecane-1,4,7-tris-[(aminocarbonyl)methyl], and 10-[(3-methoxyphenyl)methyl]-1,4,7,10-tetraazaciclododecane-1,4,7-triacetic acid or a physiologically acceptable salt thereof.

3. The method of claim 1 for the Magnetic Resonance Imaging of citrate, wherein said paramagnetic chelate complex is the gadolinium complex of 10-[(3-methoxyphenyl) methyl]-1,4,7,10-tetraazacyclododecane-1,4,7-tris-[(aminocarbonyl)methyl]chelating ligand or a physiologically acceptable salt thereof).

4. The method of claim 1 for the Magnetic Resonance Imaging of tartrate, wherein said paramagnetic chelate complex is the gadolinium complex of 10-[(3-methoxyphenyl) methyl]-1,4,7,10-tetraazacyclododecane-1,4,7-triacetic acid or a physiologically acceptable salt thereof.

5. The method of claim 2 for the detection of brain tumors.

6. The method of claim 3 for the detection of prostatic carcinoma.

7. The method of claim 1 wherein the paramagnetic ion is selected from the group consisting of: gadolinium (III), iron (II), iron (III), manganese (II), manganese (III), chromium (III), cobalt (III), copper (II), nickel (II), dysprosium (III), erbium (III), terbium (III), holmium (III), thulium (III), ytterbium (III), europium (II) and europium (III).

8. The method of claim 7 wherein the paramagnetic ion is Gadolinium (III), manganese (II) or manganese (III).

9. A compound which is selected from: 10-[(3-methoxyphenyl)methyl]-1,4,7,10-tetraazacyclododecane-1,4,7-tris-[(aminocarbonyl)methyl], the gadolinium complex thereof optionally in form of the ternary complex with citrate, 10-[(3-methoxyphenyl)methyl]-1,4,7,10-tetraazacyclododecane-1,4,7-triacetic acid and the gadolinium complex thereof.

10. A pharmaceutical composition comprising, together with a physiologically tolerable carrier, a compound of claim 9 or a physiologically acceptable salt thereof.

* * * * *